United States Patent
Comeau

(10) Patent No.: US 11,769,105 B2
(45) Date of Patent: *Sep. 26, 2023

(54) SYSTEM AND METHODS FOR NETWORK-IMPLEMENTED CANNABIS DELIVERY AND DRIVER RELEASE OF FUNDS

(71) Applicant: PELICAN DELIVERS, INC., Silverdale, WA (US)

(72) Inventor: David Comeau, Bremerton, WA (US)

( * ) Notice: Subject to any disclaimer, the term of this patent is extended or adjusted under 35 U.S.C. 154(b) by 36 days.

This patent is subject to a terminal disclaimer.

(21) Appl. No.: 17/573,446

(22) Filed: Jan. 11, 2022

(65) Prior Publication Data

US 2022/0129842 A1 Apr. 28, 2022

Related U.S. Application Data

(63) Continuation of application No. 16/822,465, filed on Mar. 18, 2020, now Pat. No. 11,222,302, which is a
(Continued)

(51) Int. Cl.
*G06Q 10/0832* (2023.01)
*G06Q 10/0835* (2023.01)
(Continued)

(52) U.S. Cl.
CPC ..... *G06Q 10/0832* (2013.01); *G06Q 10/0833* (2013.01); *G06Q 10/08355* (2013.01); *G06Q 20/102* (2013.01); *G06Q 20/12* (2013.01); *G06Q 20/145* (2013.01); *G06Q 20/3224* (2013.01); *G06Q 20/4014* (2013.01);
(Continued)

(58) Field of Classification Search
CPC .......... G06Q 20/145; G06Q 20/03224; G06Q 20/4014; G06Q 20/40145; G06Q 30/0282; G06Q 30/0607; G06Q 30/0641; G06Q 30/00; G06Q 10/0832; G06Q 10/0833;
(Continued)

(56) References Cited

U.S. PATENT DOCUMENTS 9,836,772 B1 * 12/2017 Rosenfeld ............ G06Q 10/083
10,621,560 B1 * 4/2020 Rickert ................... H04W 4/60
(Continued)

OTHER PUBLICATIONS

Tim Bingham, ""Silk Road", the virtual drug marketplace: Single case study of user experiences", published by Elsevier, 2013 (Year: 2013).*
(Continued)

*Primary Examiner* — Omar Zeroual
(74) *Attorney, Agent, or Firm* — Galvin Patent Law LLC; Brian R. Galvin

(57) ABSTRACT

A system and methods for network-enabled cannabis product delivery and driver release of funds, comprising at least a plurality of network-enabled portals for data entry, legality and identification checks, and more, allowing a user to order delivery of cannabis products from local retailers using third-party drivers that register with the system, for compensation, and allowing for feedback and automated communication between a retailer, driver, and customer using the system, with a driver being able to release funds to a retail outlet after pickup of the order.

8 Claims, 14 Drawing Sheets

Related U.S. Application Data continuation-in-part of application No. 16/366,232, filed on Mar. 27, 2019, now Pat. No. 11,222,301, which is a continuation of application No. 16/179,333, filed on Nov. 2, 2018, now Pat. No. 10,255,578.

(60) Provisional application No. 62/898,999, filed on Sep. 11, 2019, provisional application No. 62/735,226, filed on Sep. 24, 2018.

(51) Int. Cl.
*G06Q 10/0833* (2023.01)
*G06Q 30/0282* (2023.01)
*G06Q 20/40* (2012.01)
*G06Q 30/0601* (2023.01)
*G07F 17/00* (2006.01)
*G06Q 20/32* (2012.01)
*G06Q 20/10* (2012.01)
*G06Q 20/14* (2012.01)
*G06Q 20/12* (2012.01)
*G06Q 30/00* (2023.01)

(52) U.S. Cl.
CPC ... *G06Q 20/40145* (2013.01); *G06Q 30/0282* (2013.01); *G06Q 30/0607* (2013.01); *G06Q 30/0641* (2013.01); *G07F 17/0092* (2013.01); *G06Q 30/00* (2013.01)

(58) Field of Classification Search
CPC .......... G06Q 10/08355; G06Q 20/102; G06Q 20/12; G07F 17/0092
See application file for complete search history.

(56) References Cited

U.S. PATENT DOCUMENTS

| | | | | |
|---|---|---|---|---|
| 11,614,334 | B2* | 3/2023 | Williams | G01C 21/343 705/338 |
| 11,615,368 | B2* | 3/2023 | Fu | G06Q 10/0833 705/333 |
| 2007/0106422 | A1* | 5/2007 | Jennings | B25J 9/0084 222/129.1 |
| 2010/0286993 | A1* | 11/2010 | Lovelace | G16H 10/60 705/14.58 |
| 2015/0254743 | A1* | 9/2015 | Dellaportas | G06Q 50/265 705/26.25 |
| 2015/0269514 | A1* | 9/2015 | Gittings | G06Q 10/0832 705/330 |
| 2016/0063435 | A1* | 3/2016 | Shah | G06Q 30/0633 705/44 |
| 2016/0267250 | A1* | 9/2016 | Reinheimer | G16H 10/60 |
| 2018/0144390 | A1* | 5/2018 | Beckford | G06Q 30/0282 |
| 2018/0276611 | A1* | 9/2018 | Dromerhauser | G06Q 10/0833 |
| 2019/0062144 | A1* | 2/2019 | Greenbaum | G07F 17/0092 |

OTHER PUBLICATIONS

Tatiana Bierut, "Exploring Marijuana Advertising on Weedmaps, a popular Online directory", published by Cross Mark in 2017 (Year: 2017).*

Patrick Bertagna, "How does a GPS tracking system work" hereinafter "Bertagna", published by EETimes, in 2010 (Year: 2010).*

Risk Minimizer, "Risky business: 3 Things to Know before getting into Cannabis Transportation", published by rout4me, in 2018 (Year: 2018).*

* cited by examiner

SYSTEM AND METHODS FOR NETWORK-IMPLEMENTED CANNABIS DELIVERY AND DRIVER RELEASE OF FUNDS

CROSS-REFERENCE TO RELATED APPLICATIONS

Priority is claimed in the application data sheet to the following patents or patent applications, the entire written description of each of which is expressly incorporated herein by reference in its entirety:
Ser. No. 16/822,465
Ser. No. 62/898,999
Ser. No. 16/366,232
Ser. No. 16/179,333
Ser. No. 62/735,226

BACKGROUND

Field of the Art

The disclosure relates to the field of delivery systems, and more particularly to the field of internet-capable ad-hoc delivery systems.

Discussion of the State of the Art

Currently it is possible in many areas of the United States and other areas of the world to order food, groceries, and other local products to be delivered from local outlets directly to your home or doorstep, through a third-party delivery service. Such services often have drivers employed by the third-party service who then agree to take orders, and deliver goods from the vendor to a customer through some manner of application or web-enabled portal. These systems often operate with the driver holding onto the funds, either physical or digital, and transferring the funds to the outlet in exchange for the order, with the customer paying the driver and driving service rather than the outlet specifically, giving the service the ability to upcharge if necessary, add any taxes or tips as appropriate, and give drivers discretion on fulfilling orders, making the driver the point of contact for the local outlet.

No such delivery system exists for cannabis products due to the legal and banking issues associated with this product. In particular, while cannabis is legal according to the laws of some states, it remains a federal crime to transport cannabis across state lines. Also due to federal regulations, banks are prohibited from opening or maintaining accounts for businesses that sell cannabis products, so payment becomes a problem in developing such a delivery service. Security of both customer and driver is also a concern.

What is needed is a cannabis delivery system and method that overcomes the legal, banking, and security concerns for customer, driver, and the cannabis business, while allowing the same functionality for funds transference with the ordering service and the driver, allowing more flexibility and control for the driving business and driver.

SUMMARY

Accordingly, the inventor has conceived and reduced to practice, a system and method for a cannabis delivery that allows for online ordering, pickup and delivery by a third party, payment transfer from a customer to a third-party delivery person, payment digitally or in cash by the third party at the cannabis business, mapping to avoid crossing of state lines, electronic payments between customer and driver, identification verification, and a rating system between customer and driver.

According to one aspect, a system and method for network-implemented cannabis delivery and driver release of funds, is disclosed, comprising at least a system for network-enabled cannabis delivery, comprising: a retailer portal comprising at least a plurality of programming instructions stored in the memory of, and operating on at least one processor of, a computer system, wherein the plurality of programming instructions, when operating on the processor, cause the computer system to: allow a retailer of cannabis to enter information comprising its location, its products, and its prices; receive orders for cannabis products from a customer; receive information about a delivery person; and a customer portal comprising at least a plurality of programming instructions stored in the memory of, and operating on at least one processor of, a computer system, wherein the plurality of programming instructions, when operating on the processor, cause the computer system to: allow the customer to enter information comprising the customer's identity and location; use the entered information to confirm that the customer is of legal age to purchase cannabis products according to the laws of the state in which the customer is located; receive an order from the customer to purchase cannabis products from the retailer; check to ensure that the amount of cannabis and the amount of the purchase are within the limits established by the laws of the state in which the customer is located; send the order to the cannabis retailer; publish the order to a plurality of delivery persons; transfer digital currency from a user to the online system, made available to a delivery person; and a delivery portal comprising at least a plurality of programming instructions stored in the memory of, and operating on at least one processor of, a computer system, wherein the plurality of programming instructions, when operating on the processor, cause the computer system to: allow the delivery person to enter information comprising the delivery person's identity and location; use the entered information to confirm that the delivery person is of legal age to purchase or deliver cannabis products according to the laws of the state in which the customer is located; allow the delivery person to accept the order for delivery; confirm that the cannabis retailer and the customer are located in the same state, and that the route between them does not cross state lines; and allow the delivery person to indicate when to transfer the digital currency initially received from a customer, to a retailer.

Further, the system comprises a method for network-enabled cannabis delivery, comprising the steps of: allowing a retailer of cannabis to enter information comprising its location, its products, and its prices, using a retailer portal; receiving orders for cannabis products from a customer, using a retailer portal; receiving information about a delivery person, using a retailer portal; allowing the customer to enter information comprising the customer's identity and location, using a customer portal; using the entered information to confirm that the customer is of legal age to purchase cannabis products according to the laws of the state in which the customer is located, using a customer portal; receiving an order from the customer to purchase cannabis products from the retailer, using a customer portal; checking to ensure that the amount of cannabis and the amount of the purchase are within the limits established by the laws of the state in which the customer is located, using a customer portal; sending the order to the cannabis retailer, using a customer portal; publishing the order to a plurality of delivery persons, using a customer portal; transfer digital currency from a user to the online system, made available to a delivery person, using a customer portal; allowing the delivery person to enter information comprising the delivery person's identity and location, using a delivery portal; using the entered information to confirm that the delivery person is of legal age to purchase or deliver cannabis products according to the laws of the state in which the customer is located, using a delivery portal; allowing the delivery person to accept the order for delivery, using a delivery portal; confirming that the cannabis retailer and the customer are located in the same state, and that the route between them does not cross state lines, using a delivery portal; and allow the delivery person to indicate when to transfer the digital currency initially received from a customer, to a retailer, using a delivery portal.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION

Figure 1:
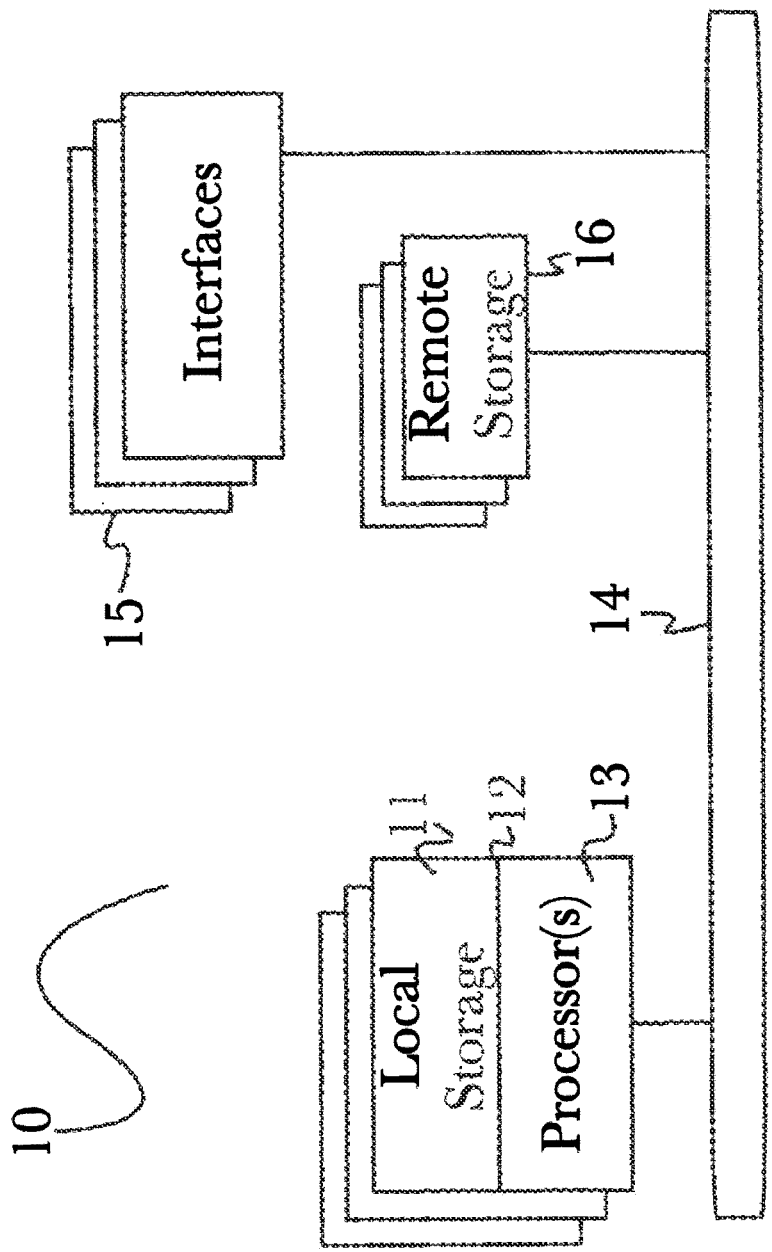
FIG. 1 is a block diagram illustrating an exemplary hardware architecture of a computing device.

The inventor has conceived, and reduced to practice, a system and method for a cannabis delivery that allows for online ordering, pickup and delivery by a third party, payment in cash by the third party at the cannabis business, mapping to avoid crossing of state lines, electronic payments between customer and driver, identification verification, and a rating system between customer and driver.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Conceptual Architecture

Figure 3:
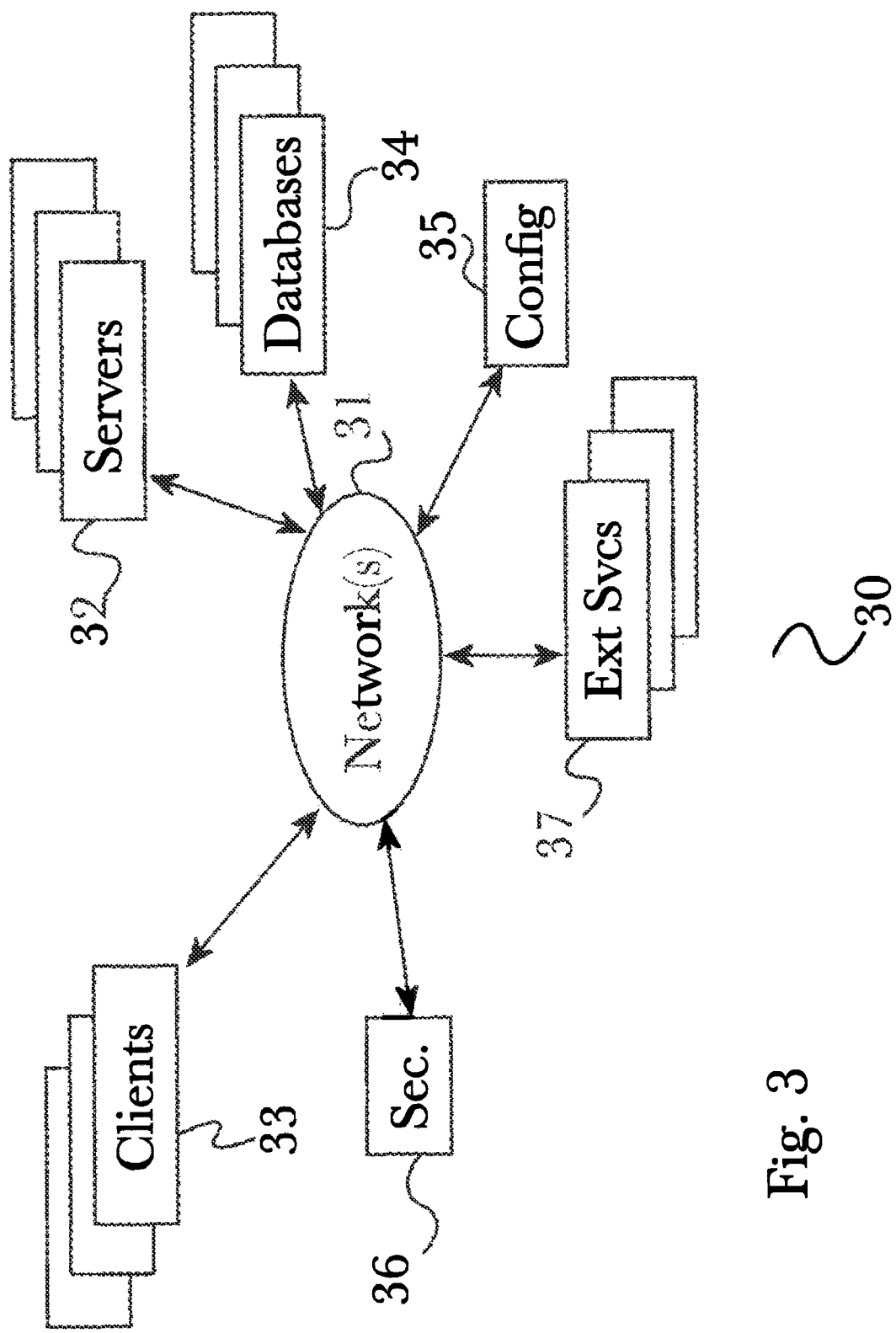
FIG. 3 is a block diagram showing an exemplary architectural arrangement of clients, servers, and external services.
Figure 4:
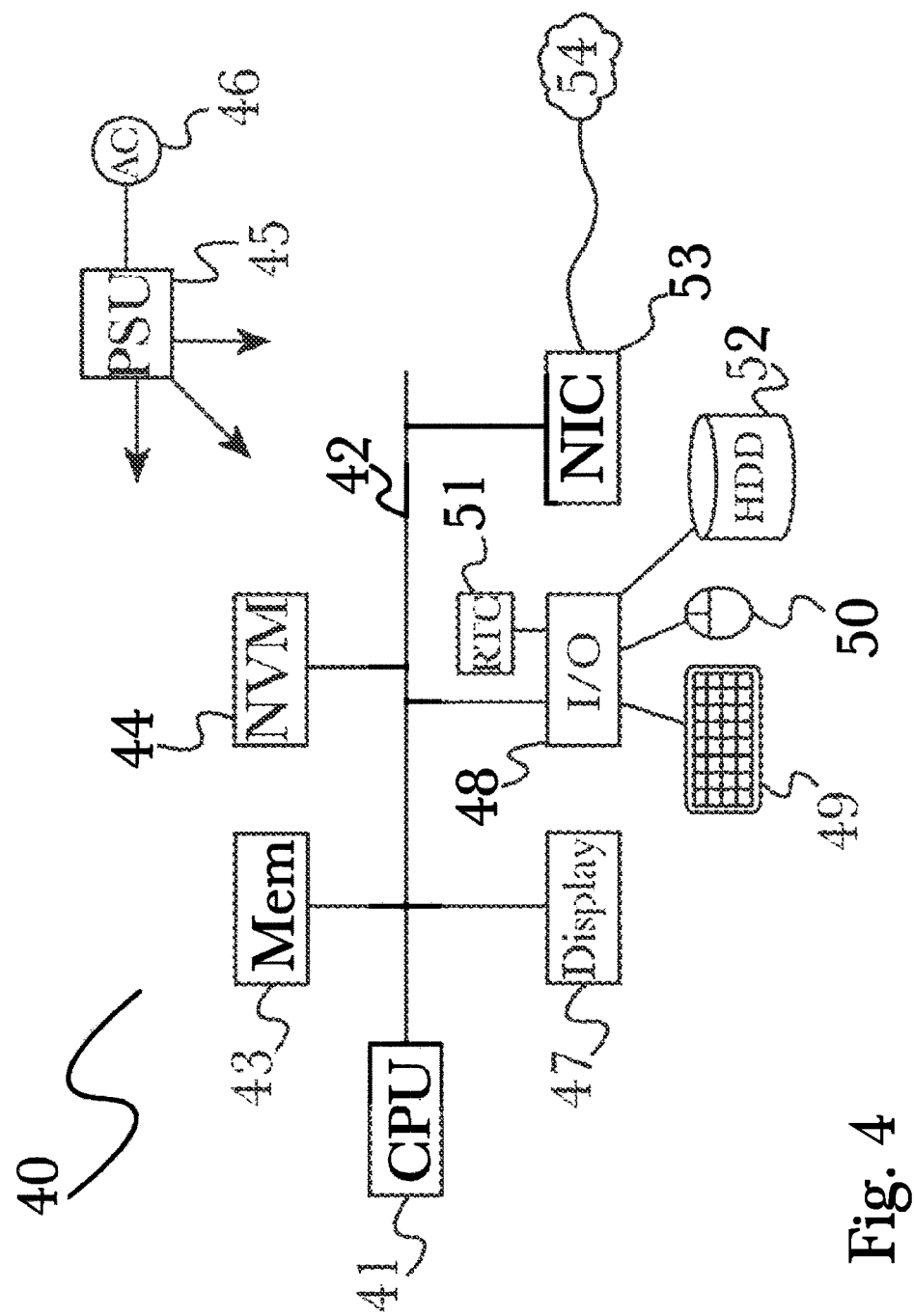
FIG. 4 is another block diagram illustrating an exemplary hardware architecture of a computing device.
Figure 5:
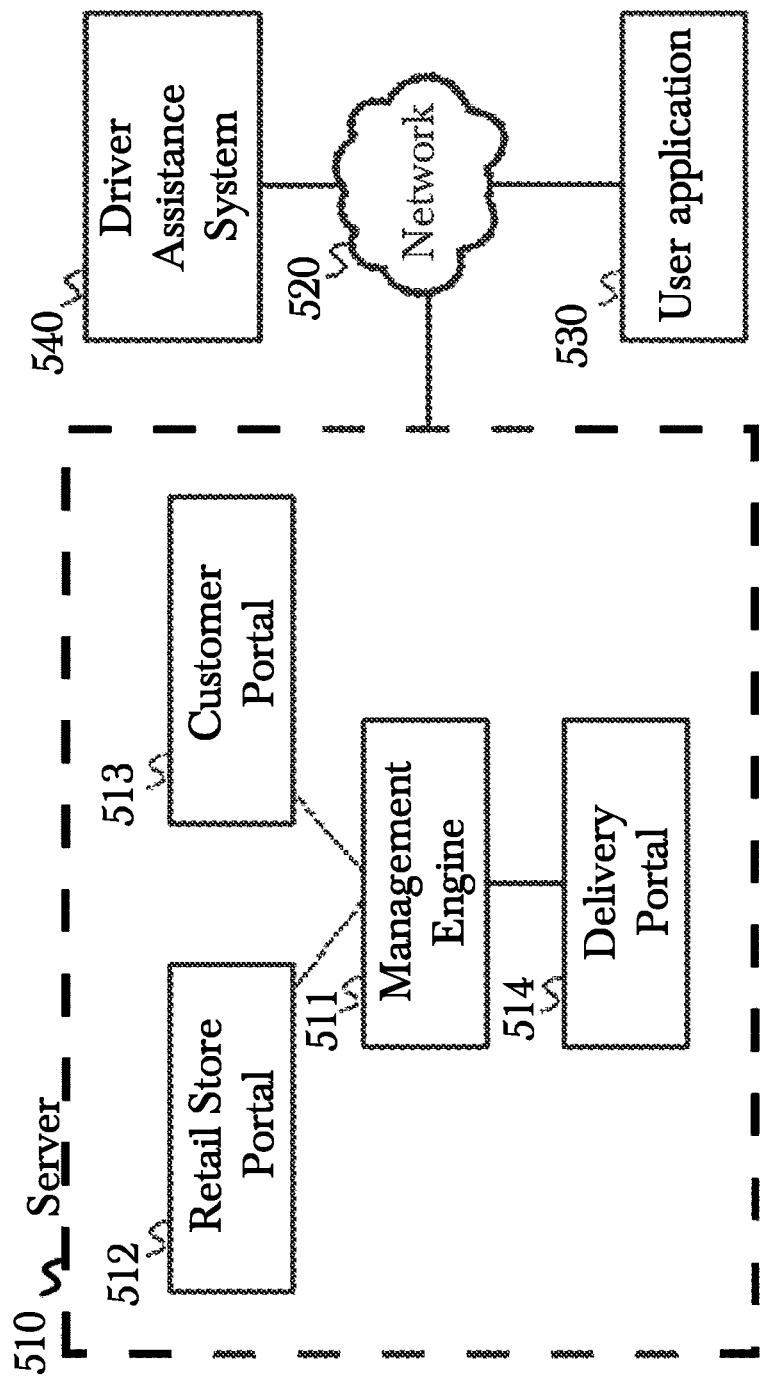
FIG. 5 is a block diagram illustrating an exemplary system architecture for network-connected components of a cannabis delivery system, according to one aspect.

FIG. 5 is a block diagram illustrating an exemplary system architecture for network-connected components of a cannabis delivery system, according to one aspect. A management engine 511 exists on a computing device as shown in FIG. 1-4, connected to a network 520 which may be a local area network (LAN) or the Internet, or some other computer network capable of transmitting data. Server software 510 contains at least a management engine 511 connected to a retail store portal 512, a customer portal 513, and a delivery portal 514, which may be accessed over a network 520 and communicate with a user application 530 which may display data from respective portals for varying types of users, whether customers 513, delivery drivers 514, or retail outlets 512. Such an application may take the form of a phone app, or an app accessed through a web browser, or in some other commonly used manner be accessible for users. Also connected to a network 520 is a Driver Assistance System 540 which is capable of assisting a driver with determining if a delivery can be made, and possibly verifying driver identity according to an aspect.

Figure 6:
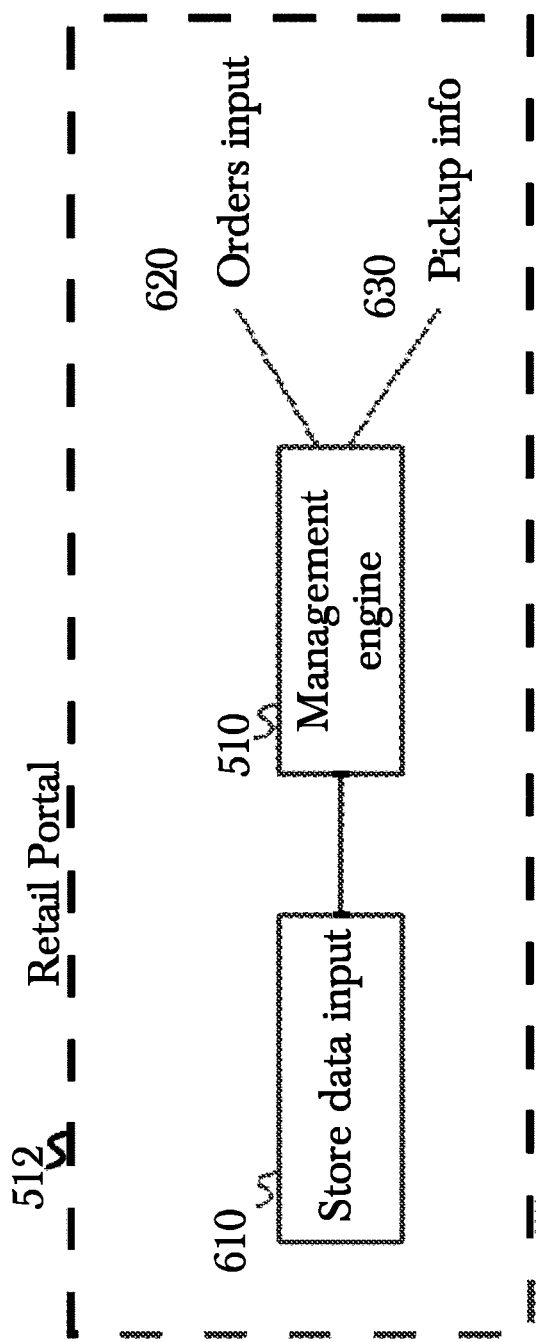
FIG. 6 is a block diagram illustrating connections between a management engine and information sources, according to a preferred aspect.

FIG. 6 is a block diagram illustrating connections between a management engine and information sources, according to a preferred aspect. Store data input 610, which may be provided from a retail store portal 512 over a network 520, communicates with a management engine 511, which may also receive information from a customer portal 513 for order information 620, and a delivery portal 514 for pickup information 630. The combination of information received from the different portals over a network 520 may allow a management engine to accurately determine the existence and status of store inventory available for delivery, customer-created orders, and driver status in delivering and fulfilling those orders, and thereby communicate back with all three entities regarding status updates as the system is used. For example a store's inventory on a retail store portal 512 may update when a user places an order 620 to reflect decreased inventory, after a driver picks it up 630, and other instances of data being communicable between the three entities may also be possible according to a preferred aspect.

Figure 7:
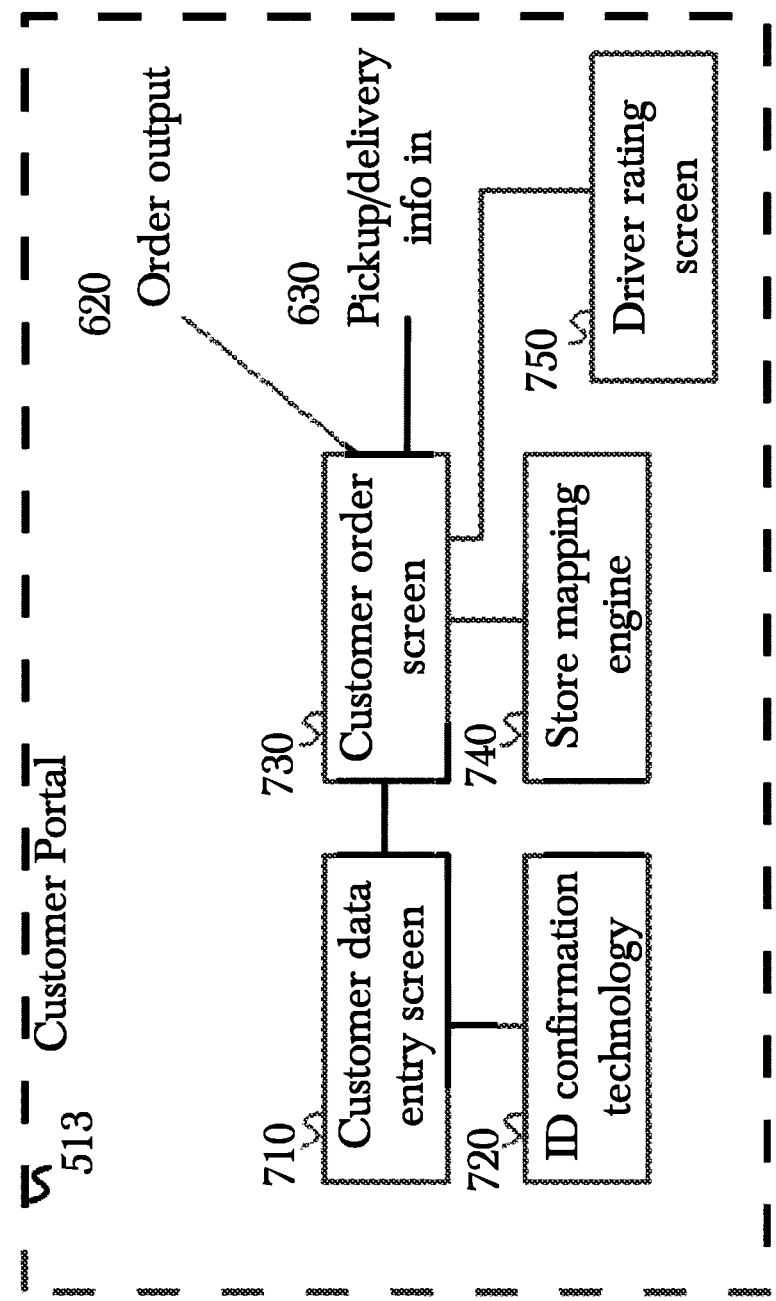
FIG. 7 is a block diagram illustrating components in a cannabis delivery system for interacting with a user, according to a preferred aspect.

FIG. 7 is a block diagram illustrating components in a cannabis delivery system for interacting with a user, according to a preferred aspect. A customer data entry screen 710 which provides options for a customer to enter their information such as shipping address, billing information, and more, according to an aspect. ID confirmation technology 720 such as password or social security lookups, or driver's license lookups, may provide methods for identity confirmation to help prevent illegal orders or orders from impersonated individuals. A customer order screen 730 exists in a management engine 511, which may have data input fields for a customer to specify what they are ordering, how much, and to what address, which may be filtered for only a store selected from a mapping engine 740 which may list close-by stores to a customer. Further, a driver rating screen 750 may exist for a customer to rate a driver's performance, for purposes such as a driver being able to read the feedback and alter their service for future customers. Order output data 620 such as the result of placing an order, or the progress of an order, may be forwarded to a customer order screen 730, as well as pickup information 630.

Figure 8:
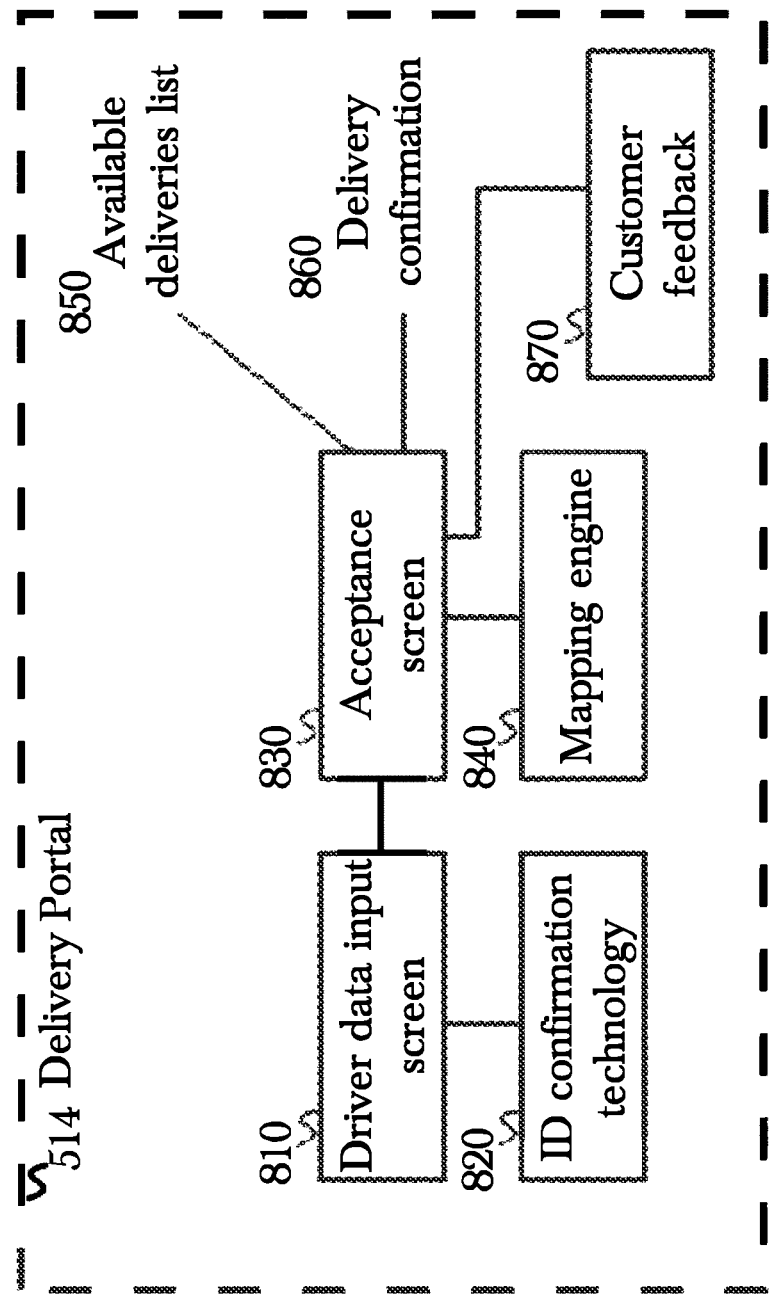
FIG. 8 is a block diagram illustrating components in a cannabis delivery system for interacting with a driver, according to a preferred aspect.

FIG. 8 is a block diagram illustrating components in a cannabis delivery system for interacting with a driver, according to a preferred aspect. A driver data input screen exists 810 on a management engine 511, which allows a driver to input their data such as a login name and password, social security information, or driver's license information, utilizing ID confirmation technology 820 to ensure that a driver is both legally able to drive as required, and legally able to handle cannabis products, as well as verifying the identity of a driver for security purposes. An acceptance screen 830 exists as well, which, after a driver enters their initial information 810 and confirms their identity 820, may allow a driver to accept a geographically viable order as determined by a mapping engine 840 which may operate separately or differently from a mapping engine for a customer 740. A driver may be able to accept an order from a distance larger or smaller than what a customer may be able to order from, for example. A list of available deliveries 850 is available to a driver through the acceptance screen 830, allowing them to pick from a variety of available, possible deliveries, and delivery confirmation 860 data is sent out from the acceptance screen 830 component to a management engine 511 for confirmation with both a user and retail outlet. Finally, the system allows the driver to provide feedback on his experience with the customer 870.

Figure 11:
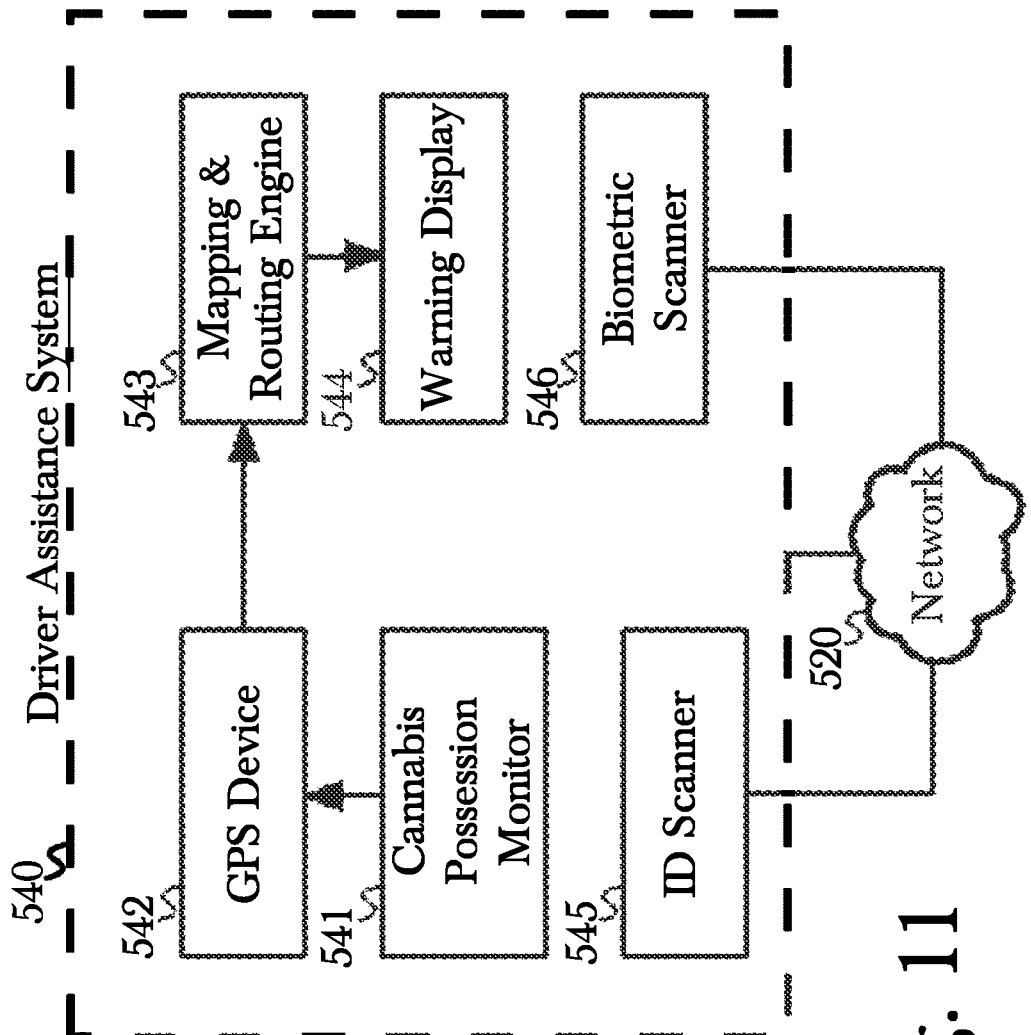
FIG. 11 is a system diagram of components in a driver assistance system, for the purpose of providing ancillary information to a driver, according to an aspect.

FIG. 11 is a system diagram of components in a driver assistance system 540, for the purpose of providing ancillary information to a driver, according to an aspect. A cannabis possession monitor 541 exists, which may take the form of a specialized container to hold delivery packages in, or a driver-entered data field on a driver application portal 514, or some other implementation of a monitoring system, according to a preferred aspect. If cannabis is detected by a cannabis possession monitor 541, a GPD device 542 which may be integrated with a driver portal 514 may inform a driver of where such things as state boundaries may be, so that a driver does not cross them and thereby potentially break local laws, using a mapping and routing engine 543. If a driver is approaching or required to approach a state line, or cross it, a warning is displayed 544, and allows the driver to avoid crossing state boundaries, or reject orders which may bring the driver past state lines if prior efforts to determine legality of an order have failed up to the point of delivery. Optionally, an ID scanner may be present 545 which may verify a driver's or customer's identity by reading a driver's license or a specialized identification card for use with the system, and a separate biometric scanner 546 may be included as well, to verify a driver's or customer's identity via fingerprint or some other biometric marker. All data from these components may be sent or retrieved via a network 520 which may allow for integration with a driver portal 514, or communication with a database for driver and mapping verification.

Figure 12:
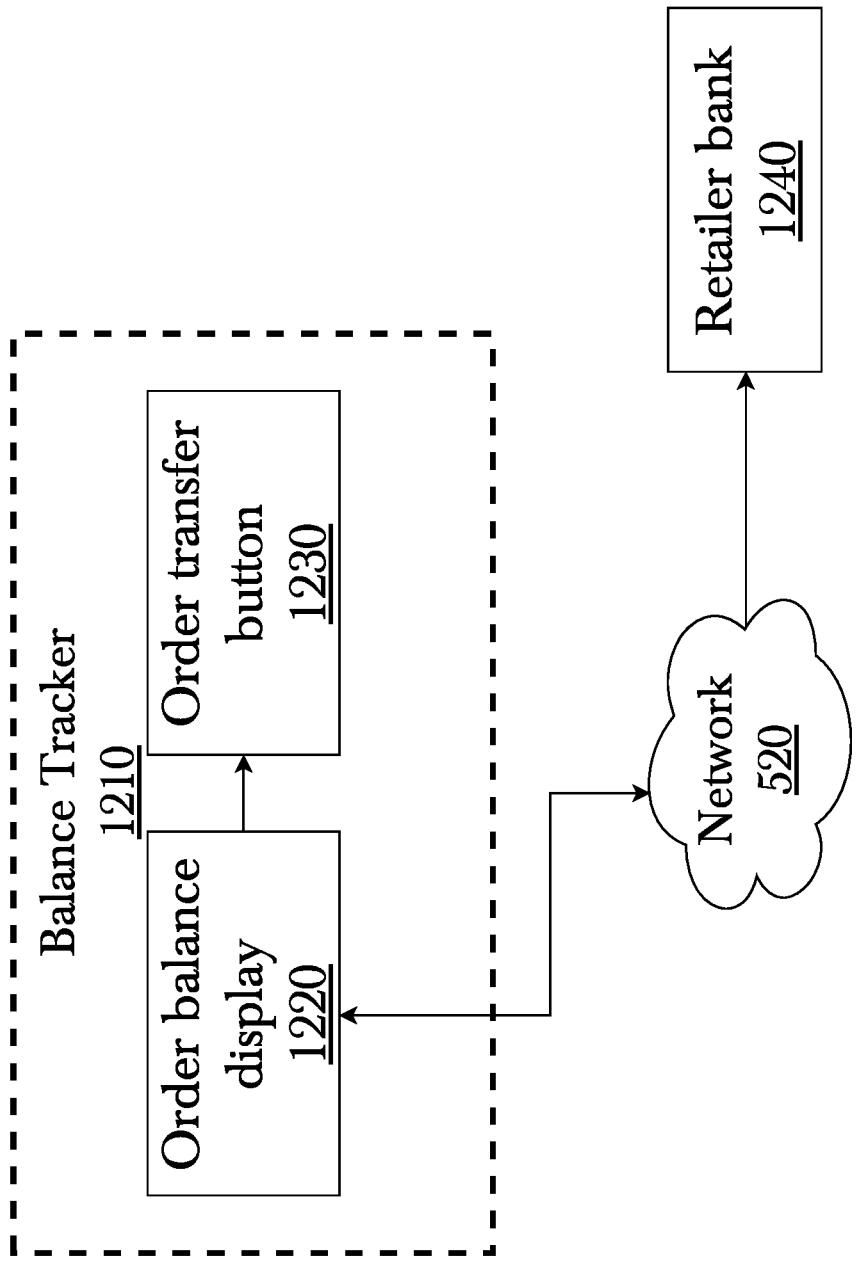
FIG. 12 is a system diagram of a balance transfer function in a cannabis delivery system, according to a preferred aspect.

FIG. 12 is a system diagram of a balance transfer function in a cannabis delivery system, according to a preferred aspect. A balance tracker 1210 exists as part of a delivery portal accessible to a delivery driver, and containing an order balance display 1220, and an order transfer button 1230, whilst connected to a network 520 and a retailer's bank 1240 or other digital money depositing feature, such as a debit or credit card payment service. The order balance display 1220 will display the total balance deposited by a user for the purpose of paying for an order that has been accepted by a delivery driver, allowing a balance transfer button 1230 which may be either a physical or on-screen button to be pressed which transfers the specified balance to the retail outlet, transferring funds over a network 520 to a retailer's banking option 1240. Such debit or credit transactions are common in the art and may be accomplished with a customized banking solution or solutions known in the art, such as PAYPAL™, direct deposits, SQUARE™, STRIPE™, or another solution as may be required.

Detailed Description of Exemplary Aspects

Figure 9:
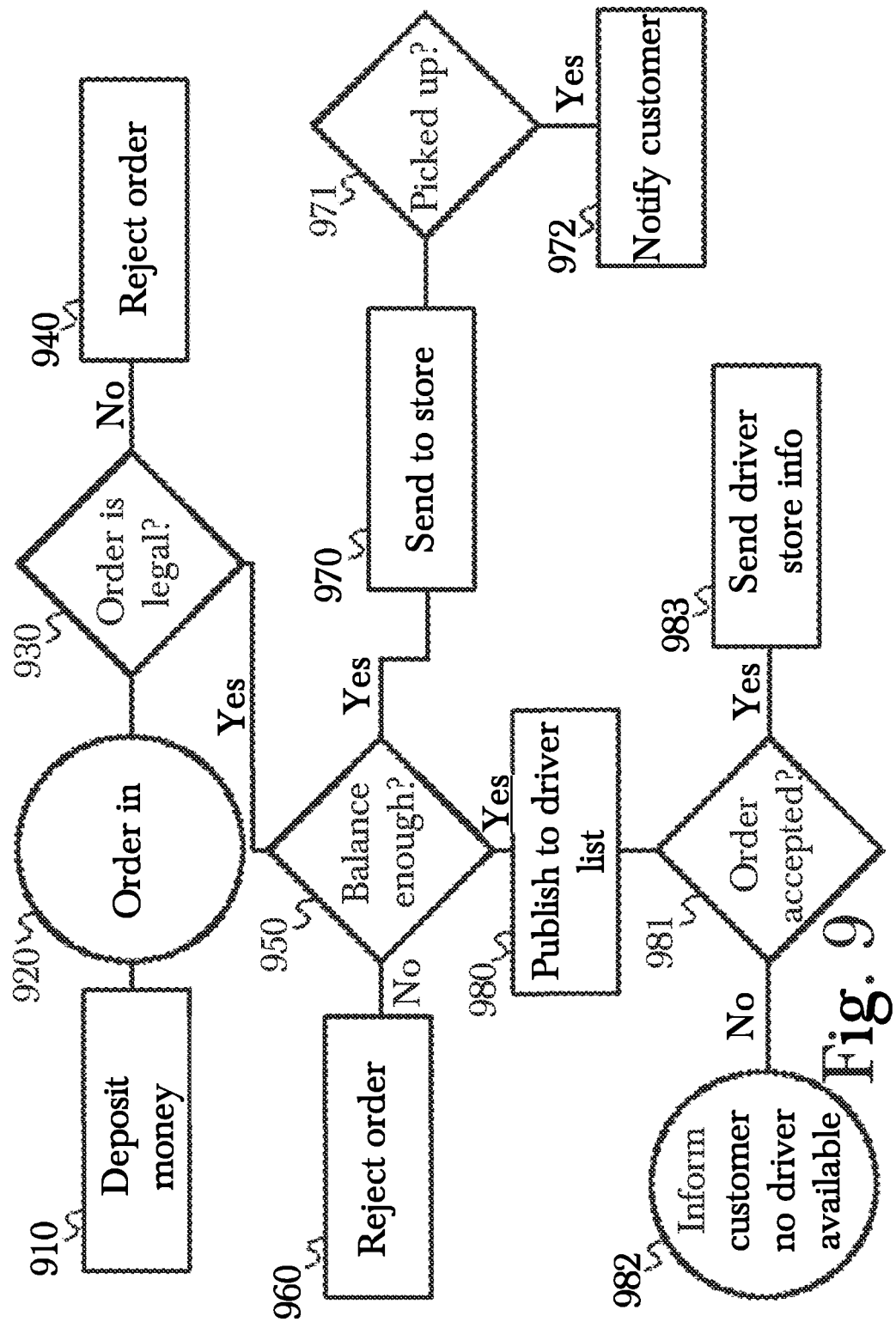
FIG. 9 is a flow diagram illustrating an exemplary method for a cannabis delivery system to operate, according to a preferred aspect.

FIG. 9 is a flow diagram illustrating an exemplary method for a cannabis delivery system to operate, according to a preferred aspect. The entrance to the system flow begins with a user depositing money 910 into a system account using a debit or credit card, or bank account information, with which they may then place an order 920 which is when a user places an order into the system through an order screen 730. The order is checked to determine if it is legal 930, using a combination of ID confirmations 720, 820, and information from order screens 730, 830, to determine legality such as if a user is of age to order cannabis products, if the product goes over state lines (which introduces many legal complications), if the driver is able to pick up the order, and more. If the order is determined to be illegal or impossible for one of these reasons or some other reason, the order is rejected 940, which is sent to the customer order screen 730 so a customer may make a different order if possible. If an order is determined to legal however, a user's balance is checked to determine if their balance is greater than the amount of product ordered 950 and order information is sent to the store or stores 970 so that retail outlets may prepare for a driver to come pick up the order. If a user's balance does not exceed the total minimum cost for an order, the order request is rejected 960 and no further action is taken in the system regarding a driver or retail outlet. If a user's balance exceeds the minimum total cost for an order, it is published to a list for drivers to view 980 and determine if they will accept the order 981. If a driver accepts an order 981, the store information is sent to the driver 983, so that the driver may go to the retail outlet and pick up the specified order. If an order is not accepted from a driver 982 after a certain period of time, a customer is informed that no driver is available, and they may have to try and place an order again at a different time. After an order's information is sent to a retail outlet 970, a management engine 511 may wait for confirmation from a retail portal 512 that the order was picked up 971, and if it is picked up, a customer is notified that their order was picked up 972 through a customer portal 514.

Figure 10:
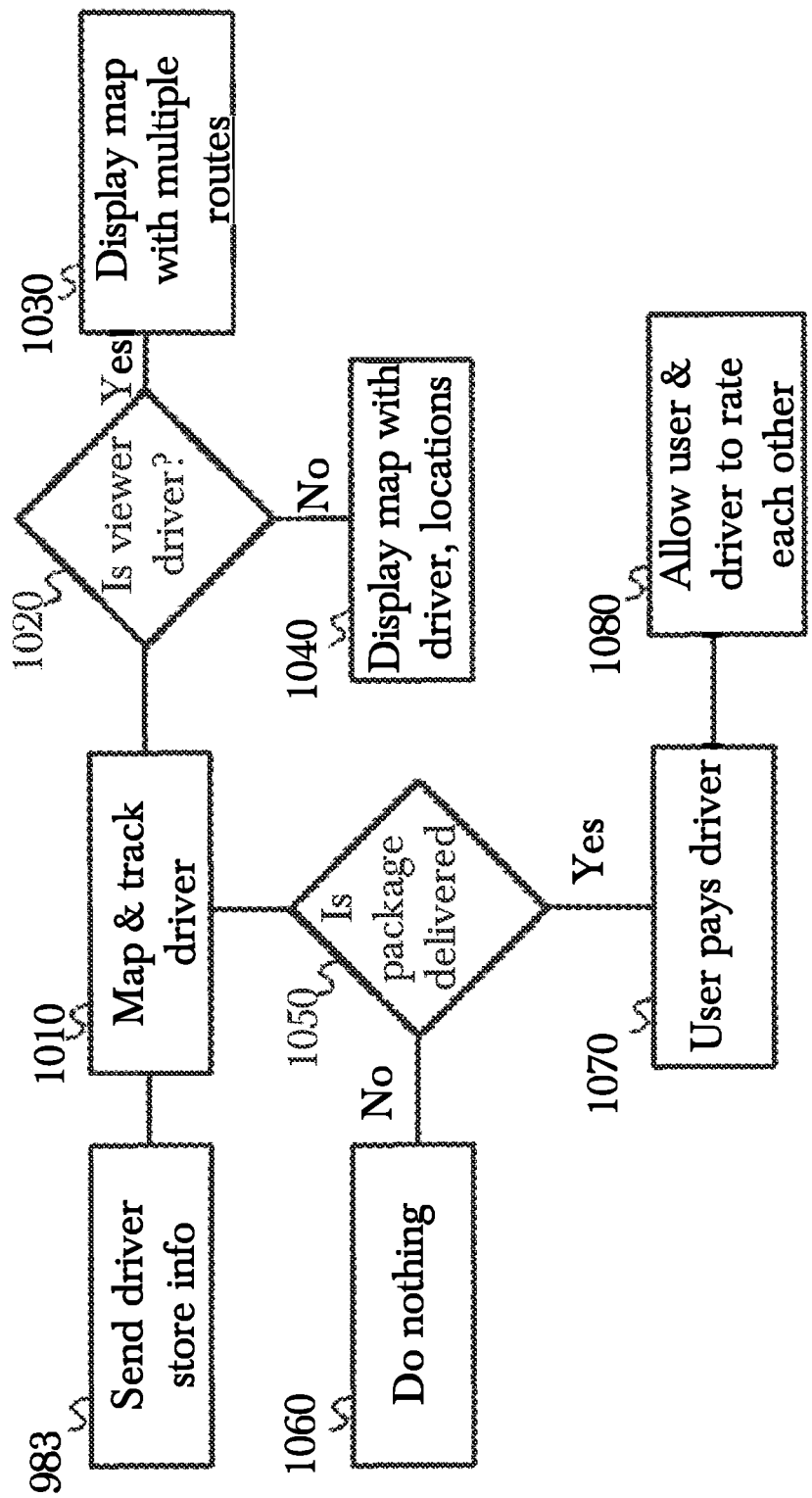
FIG. 10 is a flow diagram illustrating an exemplary method for a cannabis delivery system to operate with driver and customer data once an order is placed, according to a preferred aspect.

FIG. 10 is a flow diagram illustrating an exemplary method for a cannabis delivery system to operate with driver and customer data once an order is placed, according to a preferred aspect. After a driver is sent the information for a store at which to pick up a delivery 983, the driver is tracked across a mapping application 1010. Upon their mapping beginning, both a client and the driver himself may use the map 1020, and if viewed by the client who placed the order, the map is displayed with the locations and driver's position marked 1040 so a user may get an idea of their progress in completing the delivery or deliveries. If the driver uses the mapping application, they may see multiple possible routes 1030, to aid their deliveries. If a package is not yet successfully delivered 1050 to a user by a driver, the system does nothing 1060, waiting for user or driver input to cause change in the system. When the delivery is completed by a driver, the user pays the driver 1070, which may include taxes, shipping fees, and a tip directly for the driver themselves, and the system allows both driver and user to rate each other 1080 on a numeric scale which may vary in scale and size according to an aspect. This rating may be visible to other drivers and customers so as to penalize poor performances, while rewarding superb delivery performances and customers who were respectful or tipped their driver well.

Figure 13:
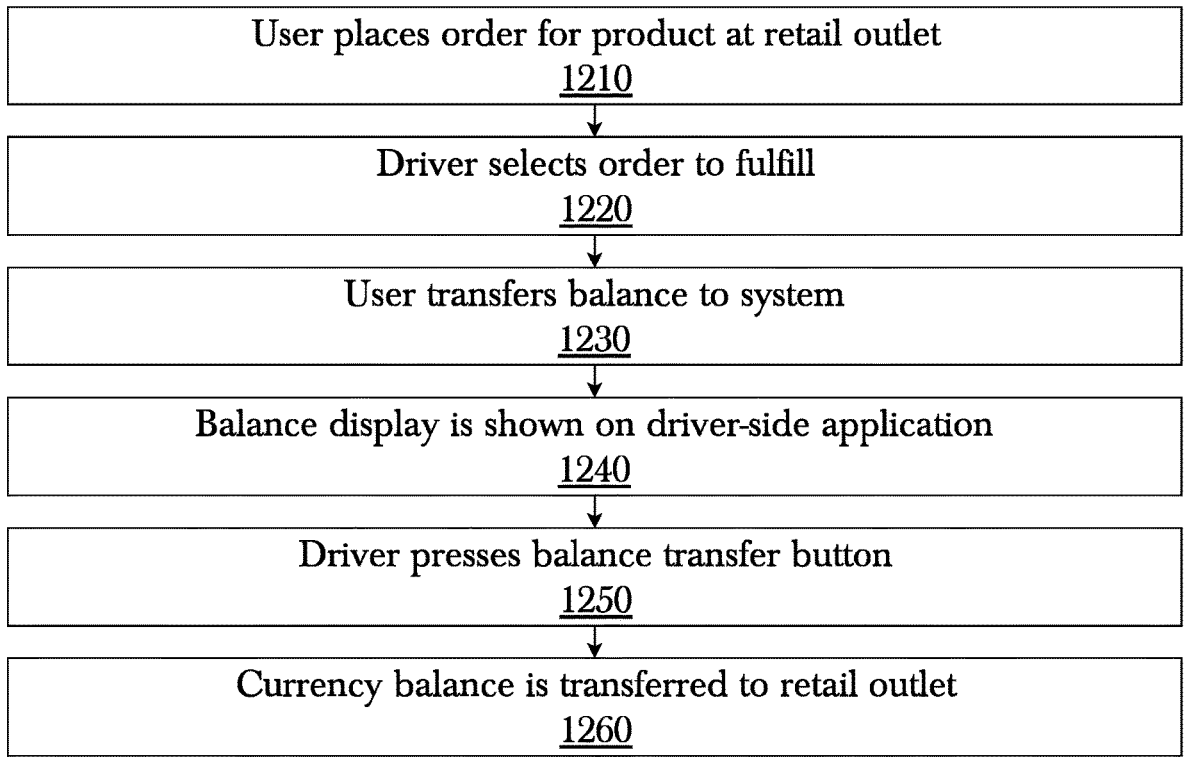
FIG. 13 is a method diagram of a balance transfer function in a cannabis delivery system, according to a preferred aspect.

FIG. 13 is a method diagram of a balance transfer function in a cannabis delivery system, according to a preferred aspect. First, a user places a delivery request or order at a retail outlet 1210, which a driver may select to fulfill 1220, through the various portals described herein. A user then must transfer a currency balance in the appropriate currency through the system 1230, which will be made available to the driver for transfer to the retail outlet, the balance being displayed on the driver's application 1240. The third-party driver may then press a balance release button 1250 when appropriate, for instance when the order is picked up from the retail outlet, which transfers the balance digitally to the retail outlet 1260 through one of many possible payment methods including direct deposit, e-checks, PAYPAL™, STRIPE™, or others.

Figure 14:
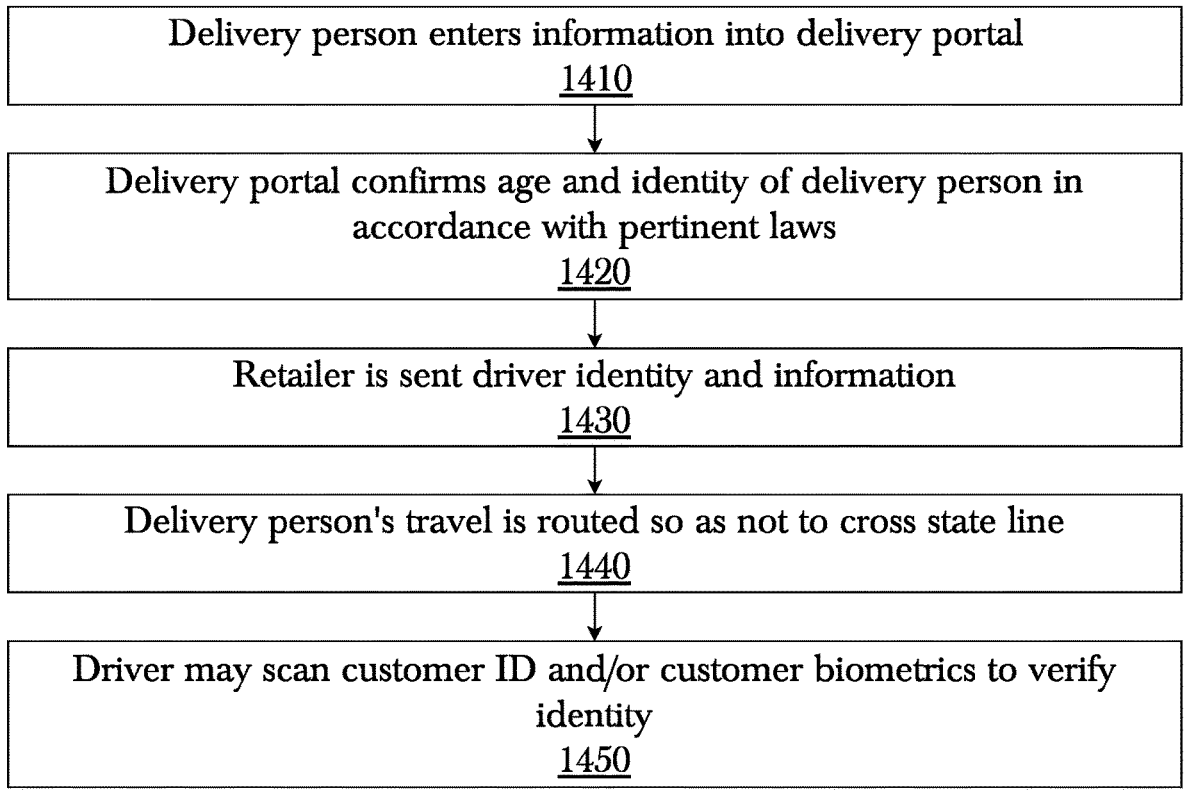
FIG. 14 is a method diagram illustrating the use of identity verification measures on both a driver and customer, and a driver's identity being made known to a retailer, according to an embodiment.

FIG. 14 is a method diagram illustrating the use of identity verification measures on both a driver and customer, and a driver's identity being made known to a retailer, according to an embodiment. A delivery person may enter their information into a delivery portal 1410, via a mobile device such as a phone or tablet, or a personal computing device, or a specialized device such as an in-car identity and shipment verification or driver assistance device. The delivery portal may then confirm the age and identity of the delivery person, in accordance with any pertinent laws 1420 including federal, state, local, or otherwise, as necessary. The identity verification may be performed with a biometric scanner or identification scanner, or some combination of both, where an identification scanner may use optical character recognition and image recognition to determine the authenticity of a government ID, such as a driver's license or state ID. This identification verification may also be integrated with local, state, federal, or organizational databases depending on the implementation. Biometric scanners may work in a similar fashion, being connected to local, state, federal, or organizational datastores for such information, so as to verify the driver's identity with authorities or within an organization, according to an exemplary embodiment. When the driver's identity is verified, they may take orders and their information is sent to the retailer via the retailer portal for the order which they have accepted 1430. This may occur over a network such as the Internet or another network suitable for transferring such data, and the delivery portal, retailer portal, and customer portal may all operate on the same server as clients, or their backend may operate on different servers entirely. After the driver's identity is entered, confirmed, and relayed to the appropriate retailer, through the use of a driver assistance system, they may then be routed for the delivery so as not to cross state lines 1440 or other legal boundaries that may be relevant for the delivery. Upon reaching the customer with the desired products, the delivery person may, before finalizing delivery, scan a customer's ID, or use a biometric scanner that may also be part of a driver assistance system, to verify the identity of the customer 1450. This may be done in a similar manner to the driver's own identity verification, and may be performed with the same or a separate device.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Referring now to FIG. 1, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 1 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 2:
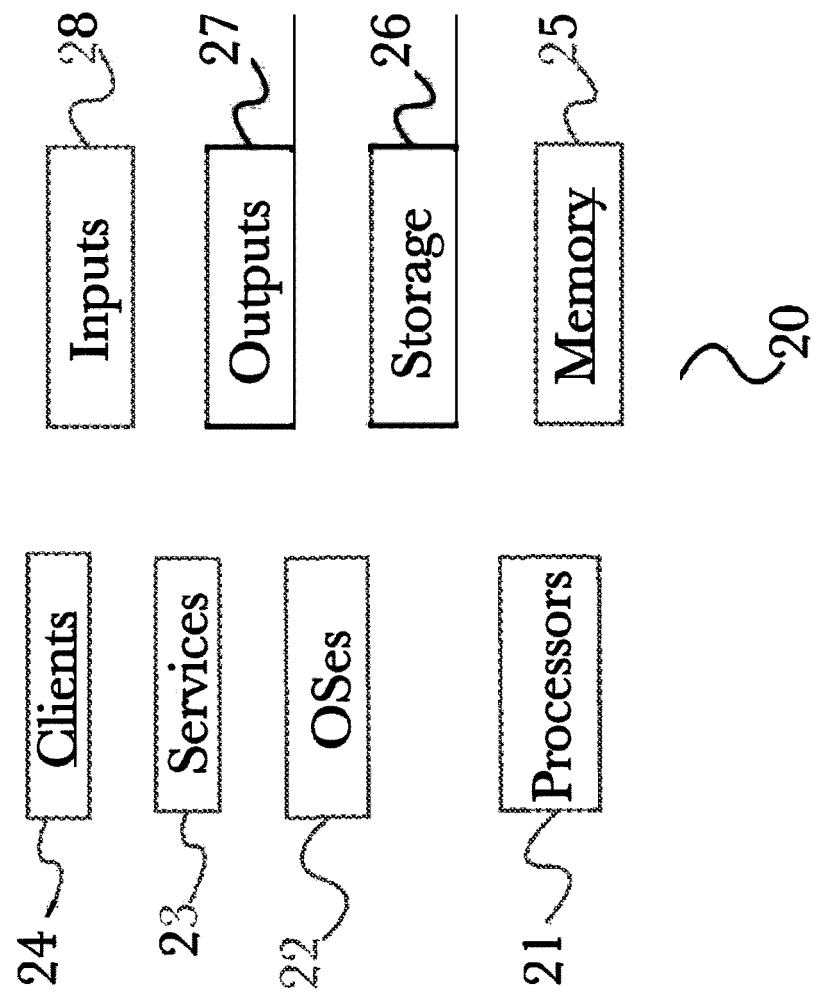
FIG. 2 is a block diagram illustrating an exemplary logical architecture for a client device.

In some aspects, systems may be implemented on a standalone computing system. Referring now to FIG. 2, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 1). Examples of storage devices 26 include flash memory, magnetic hard drive, CD-ROM, and/or the like.

In some aspects, systems may be implemented on a distributed computing network, such as one having any number of clients and/or servers. Referring now to FIG. 3, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 2. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some aspects, clients 33 or servers 32 (or both) may make use of one or more specialized services or appliances that may be deployed locally or remotely across one or more networks 31. For example, one or more databases 34 may be used or referred to by one or more aspects. It should be understood by one having ordinary skill in the art that databases 34 may be arranged in a wide variety of architectures and using a wide variety of data access and manipulation means. For example, in various aspects one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

FIG. 4 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for network-enabled cannabis delivery and driver release of funds, comprising:
 a first computing device comprising a first memory and a first processor;
 a retailer portal comprising a first plurality of programming instructions stored in the first memory which, when operating on the first processor, causes the first computing device to:
  receive orders for cannabis products from a customer; and
  receive information about a delivery person;
 a customer portal comprising a second plurality of programming instructions stored in the first memory which, when operating on the first processor, causes the first computing device to:
  allow the customer to enter customer information comprising the customer's identity, age, and address;
  automatically verify that the customer is of legal age to purchase cannabis products according to the laws of the state in which the customer is located by comparing the customer information to a database of state laws;
  receive an order from the customer to purchase cannabis products from the retailer, the order comprising an amount of cannabis;

automatically verify that the amount of cannabis is within a limit established by the laws of the state in which the customer is located by comparing the retailer's address to the database of state laws;
automatically verify that the customer and retailer are located in the same state by comparing the customer address and the retailer address;
if the order passes both verifications, send the order to the cannabis retailer; and
publish the order simultaneously to a plurality of delivery persons; and
transfer digital currency from a user account to the driver portal;
a delivery portal comprising a third plurality of programming instructions stored in the first memory which, when operating on the first processor, causes the first computing device to:
allow the delivery person to enter delivery information comprising the delivery person's identity and location;
automatically verify that the delivery person is of legal age to purchase or deliver cannabis products according to the laws of the state in which the customer is located by comparing the delivery information to the database of state laws;
allow the delivery person to accept the order for delivery;
when the order is accepted, automatically calculate, using a mapping engine, a route from the retailer address to the customer address that does not cross state lines; and
allow the delivery person to indicate when to transfer the digital currency initially received from a customer, to a retailer, by pressing a currency transfer button; and
a driver assistance system comprising:
a container configured to store the cannabis products placed into the container;
a global positioning system device attached to the container;
a second computing device comprising a second memory and a second processor; and
a mapping and routing engine comprising a fourth plurality of programming instructions stored in the second memory which, when operating on the second processor, causes the second computing device to:
connect with the driver portal via the Internet;
retrieve the route from the delivery portal;
periodically determine a location of the container using the global positioning system device;
determine if the container approaches a state line using global positioning system; and
provide a warning if the container approaches a state line.

2. The system of claim 1, wherein the customer portal, delivery portal, and retail portal are all located on a server or network of servers, and are accessible through the Internet.

3. The system of claim 1, further comprising an identification scanner configured to:
scan identification presented by the customer; and
confirm the identity of the customer by comparing the image of the identification or its text with an appropriate database.

4. The system of claim 1, further comprising a biometric scanner configured to:
scan the face, iris, or fingerprint of the customer; and
confirm the identity of the customer by comparing the image of the face, iris, or fingerprint with an appropriate database.

5. A method for network-enabled cannabis delivery and driver release of funds, comprising the steps of:
using a retailer portal operating on a first computing device to perform the steps of:
allowing a retailer of cannabis to enter retailer information comprising its address, its products, and its prices, using a retailer portal;
receiving orders for cannabis products from a customer, using the retailer portal;
receiving information about a delivery person, using the retailer portal;
using a customer portal operating on the first computing device to perform the steps of:
allowing the customer to enter customer information comprising the customer's identity, age, and address, using a customer portal;
automatically verifying that the customer is of legal age to purchase cannabis products according to the laws of the state in which the customer is located by comparing the customer information to a database of state laws, using the customer portal;
receiving an order from the customer to purchase cannabis products from the retailer, using the customer portal, the order comprising an amount of cannabis;
automatically verifying that the amount of cannabis is within a limit established by the laws of the state in which the customer is located, using the retailer portal, by comparing the retailer's address to the database of state laws;
automatically verify that the customer and retailer are located in the same state by comparing the customer address and the retailer address;
when the order passes both verifications, sending the order to the: cannabis retailer via the retailer portal;
publishing the order simultaneously to a plurality of delivery persons, using a delivery portal;
transferring digital currency from a user account to the driver portal, using the customer portal;
allowing each of the delivery person to enter delivery information comprising the delivery person's identity and location;
automatically verifying that the delivery person is of legal age to purchase or deliver cannabis products according to the laws of the state in which the customer is located, using the delivery portal by comparing the delivery information to the database of state laws;
allowing the delivery person to accept the order for delivery, using the delivery portal; when the order is accepted, automatically calculate, using a mapping engine, a route from the retailer address to the customer address that does not cross state lines;
allowing the delivery person to indicate when to transfer the digital currency initially received from a customer, to a retailer, using the delivery portal; and
using a driver assistance system to assist the one delivery person in avoiding crossing of state lines, the driver assistance system comprising:

a container configured to store the cannabis products placed into the container;
a global positioning system device attached to the container; and
a second computing device comprising a second memory and a second processor;

a mapping and routing engine comprising a fourth plurality of programming instructions which, when operating on the second processor, causes the second computing device to perform the steps of:
connecting with the driver portal via the Internet;
retrieving the route from the delivery portal;
periodically determining a location of the container using the global positioning system device;
determine when the container approaches a state line using global positioning system; and
providing a warning when the container approaches a state line.

6. The method of claim 5, wherein the customer portal, delivery portal, and retail portal are all located on a server or network of servers, and are accessible through the Internet.

7. The method of claim 6, further comprising the steps of using an identification scanner to:
scan identification presented by the customer; and
confirm the identity of the customer by comparing the image of the identification or its text with a database.

8. The method of claim 6, further comprising the steps of using a biometric scanner configured to:
scan the face, iris, or fingerprint of the customer; and
confirm the identity of the customer by comparing the image of the face, iris, or fingerprint with a database.

* * * * *